(12) United States Patent
Pusey et al.

(10) Patent No.: US 7,291,459 B2
(45) Date of Patent: Nov. 6, 2007

(54) NUCLEIC ACID DETECTOR AND METHOD OF DETECTING TARGETS WITHIN A SAMPLE

(75) Inventors: Marc L. Pusey, Huntsville, AL (US); Krishnan K. Chittur, Huntsville, AL (US); Jeffrey J. Dowell, Laceys Spring, AL (US); Joseph D. Ng, Huntsville, AL (US)

(73) Assignee: University of Alabama at Huntsville, Huntsville, AL (US)

( * ) Notice: Subject to any disclaimer, the term of this patent is extended or adjusted under 35 U.S.C. 154(b) by 454 days.

(21) Appl. No.: 10/315,826

(22) Filed: Dec. 10, 2002

(65) Prior Publication Data

US 2004/0110141 A1 Jun. 10, 2004

(51) Int. Cl.
*C12Q 1/68* (2006.01)
(52) U.S. Cl. .......................................................... 435/6
(58) Field of Classification Search .................... None
See application file for complete search history.

(56) References Cited

U.S. PATENT DOCUMENTS

| | | | |
|---|---|---|---|
| 5,770,365 A | 6/1998 | Lane et al. | |
| 5,876,930 A | 3/1999 | Livak et al. | |
| 5,925,517 A | 7/1999 | Tyagi et al. | |
| 6,177,243 B1 | 1/2001 | Albagli et al. | |
| 6,235,480 B1 | 5/2001 | Shultz et al. | |
| 6,258,569 B1 | 7/2001 | Livak et al. | |
| 6,277,607 B1 | 8/2001 | Tyagi et al. | |
| 6,316,200 B1 | 11/2001 | Nadeau et al. | |
| 6,355,421 B1 * | 3/2002 | Coull et al. | 435/6 |
| 6,365,729 B1 | 4/2002 | Tyagi et al. | |
| 6,380,377 B1 | 4/2002 | Dattagupta | |
| 6,403,319 B1 | 6/2002 | Lizardi et al. | |
| 2005/0026284 A1 * | 2/2005 | Kudlicki et al. | 435/455 |

FOREIGN PATENT DOCUMENTS

WO  WO 01/94625 A2 * 12/2001

OTHER PUBLICATIONS

Dynal. Biomagnetic Techniques in Molecular Biology. 1995. p. 35 and 41.*
Kaboev, Luchkina, Tretiakov and Bahrmand; PCR hot start using primers with structure of molecular beacons (hairpin-like structure); Nucleic Acids Research, 2000, 2 pgs., vol. 28 No. 21, Oxford University Press.
Riccelli, Merante, Leung, Bortolin, Zastawny, Janeczko and Benight, Hybridization of single-stranded DNA targets to immobilized complementary DNA probes: comparison of hairpin versus linear capture probes, Nucleic Acids Research, 2001, 9 pgs., vol. 29 No. 4, Oxford University Press.
Bordoni, Consolandi, Castiglioni, Bustl, Bernardi, Battaglia and De Bellis, Investigation of the multiple anchors approach in oligonucleotide microarray preparation using linear and stem-loop structured probes, Nucleic Acids Research, 2002, 7 pgs., vol. 30 No. 8, Oxford University Press.
Broude, Stem-looop oligonucleotides: a robust tool for molecular biology and biotechnology, TRENDS in Biotechnology, Jun. 2002, 8 pgs, vol. 20 No. 6.

* cited by examiner

*Primary Examiner*—Gary Benzion
*Assistant Examiner*—Heather Calamita
(74) *Attorney, Agent, or Firm*—Alston & Bird LLP (57) ABSTRACT

A nucleic acid detector and a method of using the detector are disclosed for detecting the presence of target nucleic acid sequences within a sample. The nucleic acid detector comprises a substrate-bound, hairpin-shaped nucleic acid captor in conjunction with a labeled universal nucleic acid detector probe. The captor has a segment that is complementary to at least a portion of the target nucleic acid and is denatured and hybridized to the target under test conditions. Hybridization of the captor to the target maintains the captor in an open conformation which exposes an end portion of the captor to the universal detector probe. The detector probe is able to hybridize with the exposed end portion of the captor if the captor has hybridized with a target. The labeled detector probe is detectable by external detection methods. Detector probes having identical universal detector probe sequences may be used to identify the presence of multiple targets having various target sequences within a sample. An assay embodying the detector and method is also contemplated.

16 Claims, 7 Drawing Sheets

STMV genomic sequence

```
1     agtaaactta ccaatcaaaa gacctaacca acaggactgt cgtggtcatt tatgctgttg
61    ggggacatag ggggaaaaca tattgccttc ttctacaaga ggccttcagt cgccataatt
121   acttggcgcc caattttggg tttcagttgc tgtttccagc tatggggaga ggtaaggtta
181   aaccaaaccg taaatcgacg ggtgacaatt cgaatgttgt tactatgatt agagctggaa
241   gctatcctaa ggtcaatccg actccaacgt gggtcagagc catacctttc gaagtgtcag
301   ttcaatctgg tattgctttt aaagtaccgg tcgggtcact attttcggca aatttccgga
361   cagattcctt tacaagcgtc acagtgatga gtgtccgtgc ttggacccag ttaacaccgc
421   cagtaaatga gtacagtttt gtgaggctga agccattgtt caagactggt gactctactg
481   aggagttcga agggcgtgca tcaaacatca acacgagc ttctgtaggg tacaggattc
541   caactaattt gcgtcagaat actgtggcag ccgacaatgt atgcgaagta agaagcaact
601   gtcgacaagt cgccttggtt atttcgtgtt gttttaactg aacctcgaca taagcctttt
661   ggatcgaagg ttaaacgatc cgctcctcgc ttgagcttga ggcggcgtat ctcttatgtc
721   aacagagaca ctttggtcta tggttgtata acaatagata gactcccgtt tgcaagatta
781   gggttaacag atcttgccgt tagtctggtt agcgcgtaac cggccttgat ttatggaata
841   gatccattgt ccaatggctt tgccaatgga acgccgacgt ggctgtataa tacgtcgttg
901   acaagtacga aatcttgtta gtgttttcc ctccacttaa atcgaaggg tttgttttgg
961   tcttcccgaa cgcatacgtt agtgtgacta ccgttgttcg aaacaagtaa aacaggaagg
1021  gggttcgaat ccctccctaa ccgcgggtaa gcggccca
```

(Seq. ID 4)

1) hypothetical protein ORF (Seq. ID 8)
3'-agacagacagacagaca-tgtataacggaagaagatgttctc-aaaatgtctgtctgtctgtc-NH-5'
(a 6.8kD protein, coded from base number 52-228)

2) capsid protein ORF (Seq. ID 9)
3'-agacagacagacagaca-atttagctgcccactgttaagctta-aaaatgtctgtctgtctgtc-NH-5'
(RNA binding protein, coded from base number 162-641)

3) pseudoknot region: (Seq. ID 10)
3'-agacagacagacagaca-gcgtatgcaatcacactgatggcaa-aaaatgtctgtctgtctgtc-NH-5'
(coded from base number 950-1059)

4) fluorescently labeled oligo: (Seq. ID 11)
5'-SH-ctgtctgtctgtctgt-SH-3'

NUCLEIC ACID DETECTOR AND METHOD OF DETECTING TARGETS WITHIN A SAMPLE

FIELD OF THE INVENTION

The invention relates to a method of detecting the presence of target nucleic acid sequences within a biological sample and to a nucleic acid probe for detecting these sequences. More specifically, the invention relates to a method of detecting target nucleic acid sequences by hybridizing the target sequences to the nucleic acid probe.

BACKGROUND OF THE INVENTION

Methods of detecting specific nucleic acids are of ever increasing importance in the field of molecular biology, diagnostics, and medicine. There currently exist several methods for detecting and identifying nucleic acids within biological samples. The reasons for selecting one method over another are varied, and include, among others, a desire to avoid radioactive materials, the cost or availability of reagents or equipment, the desire to minimize the time spent or the number of steps, the accuracy or sensitivity for a certain application, the ease of analysis, or the ability to automate the process.

The detection of specific nucleic acids may constitute a portion of a process or an end in itself. There are many applications for the detection of nucleic acids in the art, and new applications are always being developed. The ability to detect and quantify nucleic acids is useful in detecting microorganisms, viruses, biological molecules, and genetic expression level assays, and thus affects many fields, including human and veterinary medicine, food processing, and environmental testing.

Perhaps the most promising use of nucleic acid detection is the identification of infectious bacterial, viral, or fungal agents within biological samples of tissue, sputum, urine, blood, semen, or saliva. Timely detection of such infectious agents gives medical professionals the ability to diagnose and treat illnesses related to the infectious agents.

A number of techniques have been developed that can detect the presence of infectious agents, including viruses, bacteria, or fungi by the presence of their DNA and RNA using molecular biology approaches. Many methods detect the DNA and RNA by hybridizing their unique nucleic acids with a labeled nucleic acid detector and measuring some aspect of the detector that changes when the detector is hybridized.

Hybridization methods depend upon knowledge of the target nucleic acid sequence. Many known nucleic acid detection techniques depend upon specific nucleic acid hybridization in which a complementary nucleic acid probe is hybridized or annealed to the nucleic acid in the sample or on a blot, and the hybridized probes are detected.

A common process for the detection of target nucleic acid takes advantage of polymerase chain reaction ("PCR"), a technique that is well known in the art. In PCR, nucleic acid primers are added to a biological sample suspected of containing a specific DNA sequence. The primers are complementary to a part of the target sequence and anneal to the denatured target if it is present within the sample. Addition of DNA polymerase extends the primer and eventually forms a DNA duplex from the initial target strand. The duplex is denatured and the process is repeated until large numbers of the target have been reproduced, which amplifies the detectability of the sequence. The amplified nucleic acid product may then be detected in a number of ways, one of which is by incorporating a labeled nucleotide into the amplified strand.

Although PCR is an effective method of assisting in the detection of a nucleic acid target having a known sequence, PCR is time consuming and adds additional complexity to the detecting method and, therefore, may not be available as a cost effective or high speed technique of testing. PCR is also subject to errors that can accumulate over progressive amplification cycles.

Alternative techniques to PCR are known that make use of dual-labeled probes known as molecular beacons. Molecular beacons maintain a closed conformation when not hybridized to a target sequence and extend in an open conformation when hybridized to a target. One end of the molecular beacon is attached to a fluorophore label, and the other end of the beacon is attached to a quencher. The beacon is initially presented in a closed conformation, where the fluorophore and quencher are adjacent to one another and tend to cancel out one another. If a target nucleic acid is present within a sample, the beacon opens and bonds to the target along the length of the target sequence. Because hybridization with a target maintains the beacon in an open conformation, the fluorophore is spaced apart from and uninhibited by the quencher, thereby fluorescing and indicating the presence of the target.

Interaction of the fluorophores and quencher molecules is often hard to detect reliably. The difference in emission between the unhybridized beacons and the hybridized beacons can sometimes be difficult to detect in the presence of background fluorescence even though molecular beacons are quite specific and able to detect sequences differing by as little as one nucleotide. Difficulty in detection makes the molecular beacons unsuitable for use in nucleic acid analysis without the use of sophisticated detection equipment.

It is desired to provide a nucleic acid detector and method of reliably detecting specific sequences of nucleic acid within a biological sample without the need to amplify the target prior to or during detection. It is desired to provide a detector and method to detect specific nucleic acid sequences that reliably indicate the presence of the target without concern of inaccuracies due to background noise. It is desired to provide a detector and method that may be used to simultaneously detect the presence of multiple targets within a sample.

BRIEF SUMMARY OF THE INVENTION

The invention is a nucleic acid detector and a method of using the detector to indicate the presence of a target in which a detector probe binds to a captor only if the captor has hybridized with a target, thereby reducing background noise, increasing ease of detection, and providing for simultaneous detection of several different targets.

The nucleic acid detector comprises a substrate-bound, hairpin-shaped nucleic acid captor that works in conjunction with a nucleic acid detector probe to detect and indicate the presence of a target within a sample. The captor has a loop segment that is complementary to at least a portion of the target nucleic acid and that is denatured and hybridized to the target under test conditions. Hybridization of the captor to the target maintains the captor in an open conformation that exposes an end portion of the captor to a detector probe. The detector probe is able to hybridize with the exposed end portion of the captor only if the captor has hybridized with a target. The detector probe is also bound to a label which is detectable by external detection methods.

In addition to the nucleic acid loop segment, the captor comprises two tail sequences that are complementary to one another and are attached to each end of the loop sequence. The two tail sequences tend to hybridize to form a stem, thereby forming the captor into a hairpin shape. The captor is attached to a substrate by a connector molecule bound to the non-loop end of the first tail. The tail segment of the captor that is not bound to the substrate is complementary to the labeled detector probe.

When the hairpin captor is denatured, the stem of the captor de-hybridizes, the hairpin opens, and the loop sequence of the captor becomes exposed. If a target nucleic acid is present within a sample, the target hybridizes with the loop sequence of the captor. The target only hybridizes with the loop region of the captor if the target contains a sequence that is complementary to a sequence found within the loop of the captor.

After the captor is exposed to a sample possibly containing the target nucleic acids, the captor is renatured by lowering the temperature of the captor or otherwise making conditions favorable for renaturing. Under such conditions, the tail segments of unhindered captors will rehybridize and the captor will return to its hairpin shape. If a target is hybridized to the captor, it becomes unfavorable for the hindered captor to return to a hairpin form.

After exposure to a sample containing possible targets, the captor is exposed to a universal detector probe. The sequence of the detector probe is complementary to the tail segment of the captor molecule which is not bound to the substrate, and tends to bond to that tail segment if the tail is exposed. If a target has hybridized with the captor, the hairpin captor will have an open conformation and the unbound tail of the captor will be free to hybridize with the detector probe. If no target has hybridized to the captor and the captor has reformed into the hairpin conformation, then the detector probe sequence is unable to bind to the closed hairpin and is washed away.

The detector probe has labels, such as fluorescent labels, attached to the detector probe sequence. Presence of the label, and therefore the target, is easily detectable using an external meter.

An assay kit may be formed by placing various clusters of captors upon corresponding regions of a substrate wherein only the loop sequences of the captors differ from cluster to cluster and wherein each of the loop sequences of a cluster is complementary to a portion of a target of interest. In this manner, the presence of multiple targets may be simultaneously detected by use of various captors upon the same substrate. The presence of targets will be indicated by the fluorescence of the substrate region corresponding to the cluster of captors that have hybridized to that target and subsequently hybridized with the detector probe.

When used as an assay, the captors of each cluster may be designed with differing loop sequences, but with the same tail sequences. Use of multiple captors having tails with identical sequences allows use of a universal detector probe that binds to any exposed tail of the captors regardless of the loop region of the captor. Thus, a universal detection probe may be used with the assay, wherein all detector probes have identical sequences. Use of a universal detection probe greatly simplifies the detection process by requiring the preparation of only a single detector probe sequence.

Thus, the detectors and method provide for detection of nucleic acid targets with less interference from background noise because detector probes are completely washed from the captors when no targets are present. This overcomes many of the complications in previous detection methods that relied upon the orientation of labeled probes rather than the presence or absence of the probes.

The detector also provides ease in detection of multiple targets when the captors are disposed as separate clusters upon the surface of a common substrate therefore allowing the simultaneous detection of multiple targets within a common sample.

BRIEF DESCRIPTION OF THE DRAWINGS

Having thus described the invention in general terms, reference will now be made to the accompanying drawings, which are not necessarily drawn to scale, and wherein:

FIG. 8 is a sequence listing taken from the Satellite Tobacco Mosaic Virus (STMV);

FIG. 9 shows sequence listings for exemplary captors and an exemplary detector probe pre-cursor in accordance with an embodiment of the invention;

DETAILED DESCRIPTION OF THE INVENTION

The invention will be described more fully hereinafter with reference to the accompanying drawings, in which some, but not all embodiments of the invention are shown. Indeed, the invention may be embodied in many different forms and should not be construed as limited to the embodiments set forth herein; rather, these embodiments are provided so that this disclosure will satisfy applicable legal requirements. Like numbers refer to like elements throughout.

Figure 1:
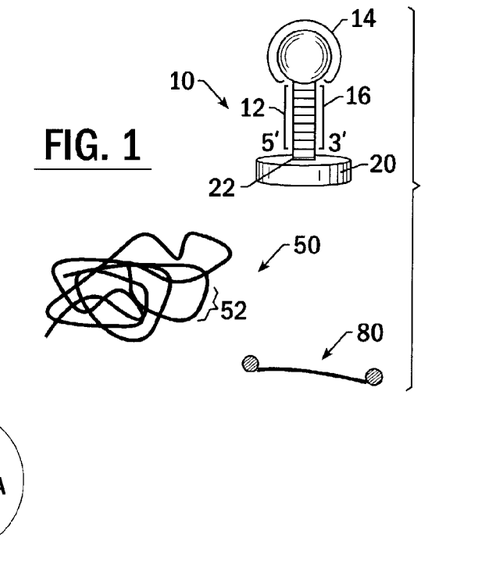
FIG. 1 is a graphic representation of a nucleic acid captor, target, and detector probe in accordance with an embodiment of the invention.

Referring generally to FIG. 1, the detector and method utilize a captor molecule 10 and a labeled detector probe 80 to determine the presence of a target nucleic acid 50 within a sample.

As used herein, the term "target" or "target nucleic acid" refers to a length of DNA, RNA, or peptide nucleic acid (PNA) to be indicated by the detector and the method of detection. The target will correspond to a bacteria, fungus, virus, or other biological agent of interest within a sample being tested. Each target contains one or more target sequences. A "target sequence" is a nucleic acid sequence having a discrete number and specific arrangement of nucleotides. It is the target sequences that are bound to detector molecules, and which thereby indicate the presence of the target.

The captor 10 is comprised of a single length of nucleic acid divided into three major regions, a first tail region 12, a loop 14, and a second tail region 16. Beginning with the 5' end of the captor 10, the first region of nucleic acid comprises a first tail sequence 12. The first tail sequence 12 is preferably between about 8 and about 20 nucleotides in length and serves to tether the captor to a substrate 20 while spacing the loop region of the captor a distance from the surface of the substrate 20. The sequence of the tail 12 is designed so that it is not complementary to the target 80, the loop 14, or any other sequences present within the testing environment (except the second tail, as discussed below).

The 3' end of the first tail 12 is connected to the 5' end of the loop sequence 14 of the captor. The loop sequence 14 of the captor 10 is complementary to a target sequence of the target 50 to be detected. The sequence to be detected is all or a portion of the nucleic acid corresponding to the presence of a specific biological substance within a sample to be analyzed. The biological substance is typically an infectious bacterial, viral, or fungal agent within a sample of body fluid, though the detector and method are equally applicable to general DNA/RNA detection in most environments. The detector may also be used for detection of PNA molecules, though PNA is not typically encountered when dealing with natural biological agents.

The sequences of target bacterial, viral, or fungal agents suspected of causing disease will be previously known from laboratory research. From each known target nucleic acid, a relatively small portion is selected and designated the target sequence 52. The length of the target sequence should be short enough that it does not unduly burden hybridization between the captor and the target and long enough to provide a target sequence that is unique to the target. Preferable target sequence lengths are between about 10 and about 40 residues, and more preferably between about 20 and 30 residues, therefore the length of the loop portion 14 will be of similar length. After a target sequence has been determined, a sequence is then derived that is complementary to the target sequence. Such a sequence may be produced in a laboratory or purchased commercially from a company such as Qiagen Operon, Alameda, Calif. The complementary sequence is used as the loop portion 14 of the captor molecule.

The 3' end of the loop 14 is connected to a second tail sequence 16. The second tail sequence 16 is complementary to the first tail sequence 12. Under conditions which are favorable to hybridization of the tail sequences 12, 16, the captor molecule 10 bends over upon itself such that the tails hybridize to form a double strand stem, with the loop 14 sequence forming a physical loop between the hybridized tails. This loop/stem combination gives the captor its characteristic hairpin shape.

Though the loop portion 14 and the tail portions 12, 16 of the captor may be selected from a range of lengths, the tail regions are preferably shorter than the loop portion. Favorable results may be obtained with various length of tail portions and loop portions, though particularly favorable results are obtained when the loop portion is at least 10 residues longer than the tail portions of the captor.

The captor 10 is bound to a substrate 20 by a linking group 22 attached to the 5' end of the first tail 12. The substrate 20 may be any substrate like glass, nylon, or other polymer that is chemically treated to introduce functionality capable of bonding with a functional group placed on the 5' end of the first tail. For example, an amine group may be used as the linking group and an aldehyde functionality may be provided to a filter paper like substrate by a simple washing with formaldehyde. If solid supports like silicon are used, additional chemistries may be required to provide the aldehyde functionality. Such methods of providing functionality are known in the art. The 5'-amine group on the captor sequence will spontaneously react with the aldehydes on the substrate via a Schiff base reaction to yield a covalent attachment.

Figure 2:
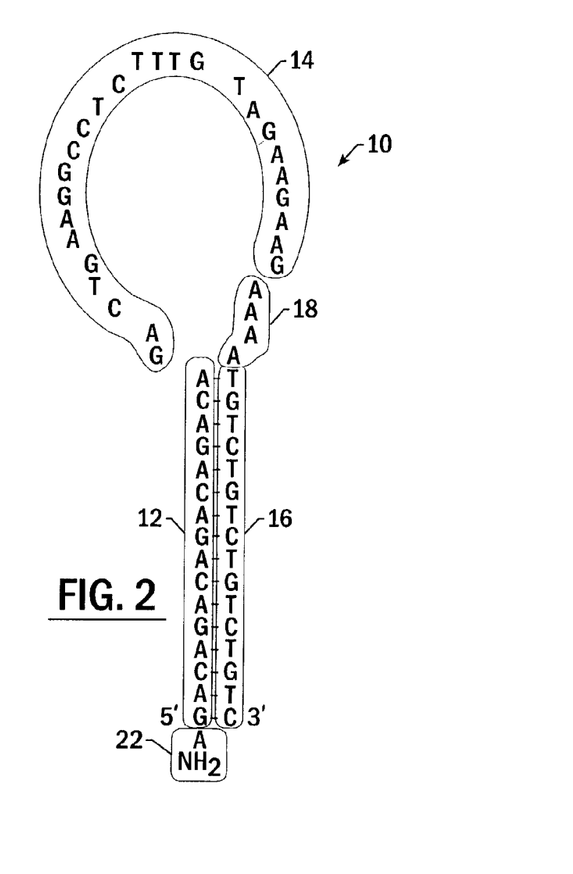
FIG. 2 is an exemplary nucleic acid sequence of a captor in accordance with an embodiment of the invention.

A spacer group 18, such as shown in FIG. 2, is an optional component of the captor 10, and may be any length sequence, preferably between 2 and 10 nucleotides, which is used to provide spacing between the loop 14 and the first tail 12 and/or the second tail 16. Because the loop 14 will be used to bind to a comparatively large target 50, and the second tail 16 will be used to bind a probe 80, the spacer group 18 is preferably placed between the loop 14 and the second tail 16 so that the loop and second tail are separated a distance by nucleotides which neither bind to the target sequence nor the probe 80. This distance lowers the chance of the bound target unintentionally preventing the probe 80 from hybridizing with the second tail 16.

Referring to FIG. 2, an exemplary captor 10 is shown having a sequence

GACTG AAGGC CTCTT TGTAG AAGAA G    (Seq. ID 1)

forming the loop portion 14 of the captor 10, a sequence

GACA GACA GACA GACA    (Seq. ID 2)

forming the first tail 12, and a sequence

TGTC TGTC TGTC TGTC    (Seq. ID 3)

forming the second tail 16. The first tail 12 is derived from four repeat GACA tetramers. The second tail 16, which is complementary to the first tail 12, is derived from four repeat CTGT tetramers. One adenosine residue and an amine group provide the linking group 22 which is used to bind the captor to a substrate. A spacer group 18, indicated here as four adenosine residues is present between the loop 14 and the second tail 16.

Figure 2A:
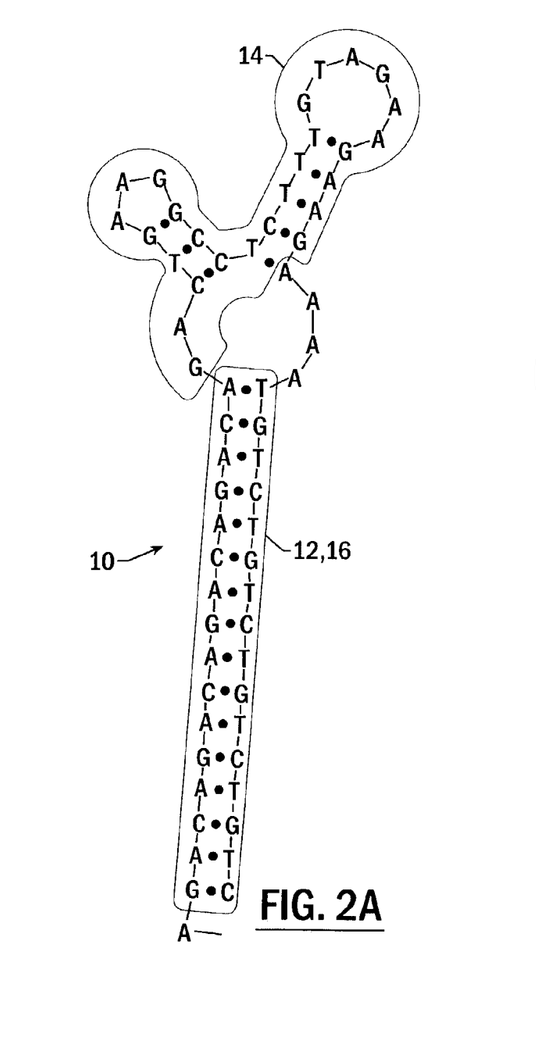
FIG. 2A is a second exemplary nucleic acid sequence of a captor in accordance with an embodiment of the invention.

Referring to FIG. 2A, it is known that the loop region of the hairpin captor 10 tends to fold in upon itself below a critical temperature to form a loop which may comprise several smaller loops. Above a critical temperature, the loop region 14 of the captor unfolds first, followed by the dehybridization of the stem region 12,16. When renatured, the tail regions first rehybridize, followed by the refolding of the loop. Thus, the folding of the loop region does not effect the operation of the captor.

Biological samples suspected of containing nucleic acid targets are treated prior to testing. Because biological samples, which are usually solutions, typically contain nucleases or other proteins and substances which could digest the target and captor sequences, the sample is preferably treated to inactivate the harmful substances prior to introduction of the captor. The sample is preferably treated with nuclease inhibiting extraction buffers. Buffers containing components such as sodium dodecyl sulfate (SDS), ethylene diamine tetraacetic acid (EDTA), dimethyl sulfoxide (DMSO), and other nuclease inhibitor molecules are commercially available. EDTA is a chelating agent and binds preferentially to divalent cations like calcium and magnesium. The majority of nucleases require $Mg^{2+}$ to be active. Thus, the addition of EDTA removes $Mg^{2+}$ and renders the nucleases inactive. SDS denatures proteins (nucleases) and renders them inactive in addition to breaking down viral capsids and bacterial membranes. DMSO helps to inhibit secondary structure formation in nucleic acids. The amount of DMSO used has to be carefully chosen to allow the hybridization of the target sequences to the captors while allowing the unhybridized captors to refold to the native state. RNAsin is commercially available from a company called Promega and inhibits nuclease activity. A preferred extraction buffer consists of 0.35 ml 25% SDS, 0.05 ml 50 mM EDTA, 0.05 ml RNAsin and 0.05 ml DMSO. Such buffers are effective nuclease inhibitors when used with samples containing target sequences in whole blood and serum, and are also effective for samples containing target sequences in urine, saliva or other body fluids. The relative amount of the different components of the buffer required for preparation of the sample will depend upon the inherent nuclease inhibition ability of the buffer and the amount of proteins within the sample. As a general guideline, proper sample preparation may be accomplished by mixing the buffer and sample in a 1:1 ratio. The nuclease inhibitors serve to maintain the viability of the target and the captor sequences during the detection method.

Figure 3:
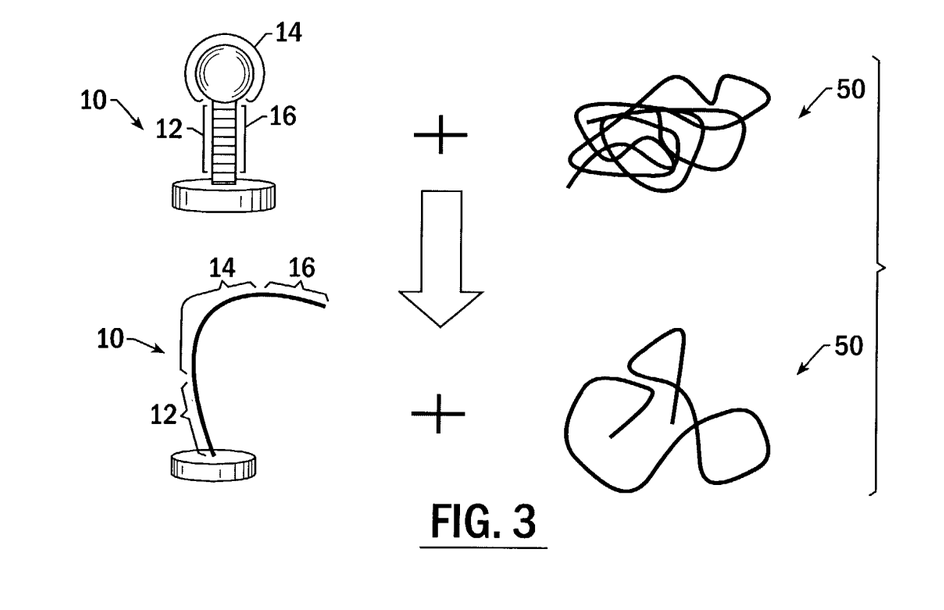
FIG. 3 is a graphic representation of nucleic acid denaturing in accordance with an embodiment of the invention.

To detect the presence of a target within the biological sample, the substrate-bound captor 10 is exposed to the target 50 in a liquid solution of the biological sample and extraction buffer. Referring to FIG. 3, the biological sample (containing the target 50, if any) and the captor 10 are heated in order to denature both of them. The size of the target and the captor will play a role in the determination of the denaturing temperature. As the captor size increases, the melting temperature of the captor also increases. With the captors we have designed and tested, the melting temperature is between 45° C. and 50° C., though higher temperatures may be used.

There are many ways to denature the target and the captor sequences but there are many advantages with using heat. It is possible to chemically denature the target and the captors but these same chemicals may later prevent the refolding of the non-hybridized captor sequences if they are still present in the reaction mixture. Heating and cooling are therefore a more reliable technique for changing the denaturing and renaturing conditions.

The captor 10 denatures by dehybridizing the second tail 16 from the first tail 12 of the hairpin. After dehybridization, the captor 10 is a single nucleic acid strand which is bound to a substrate by one end. The complementary loop sequence 14 thus becomes available for binding with potential target sequences.

Figure 4:
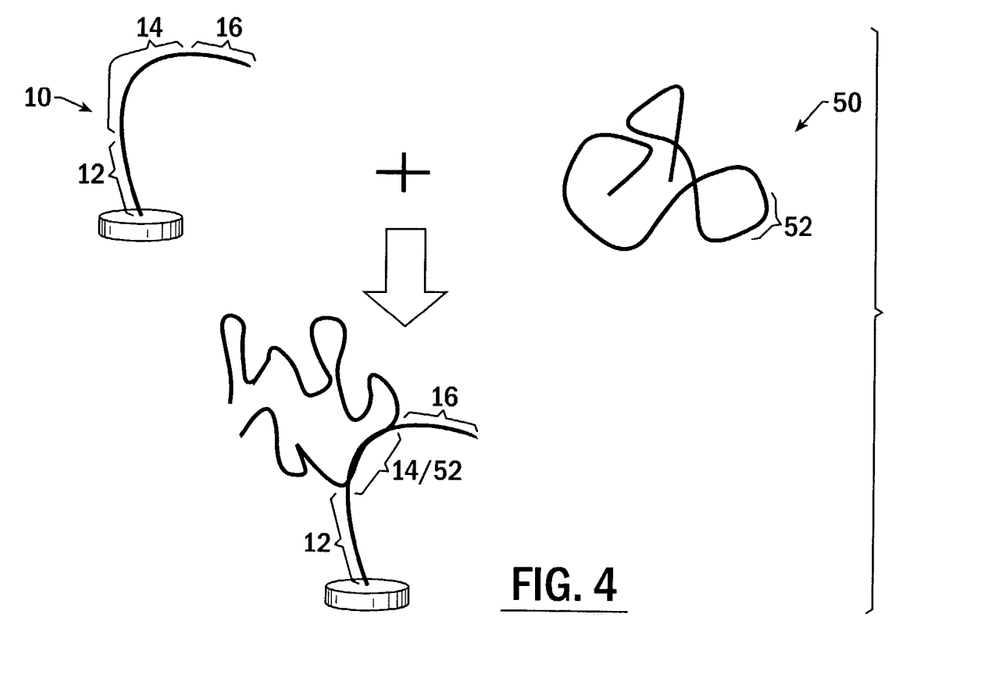
FIG. 4 is a graphic representation of hybridization between a target and a captor in accordance with an embodiment of the invention.

Referring to FIG. 4, when the denatured target 50 encounters the denatured captor 10, hybridization occurs between the loop region 14 of the captor and the target sequence 52 of the target 50. In a denaturing environment containing multiple targets and captors, an equilibrium state is reached having a number of closed captors, open captors, target-bound captors, and free targets.

Figure 5:
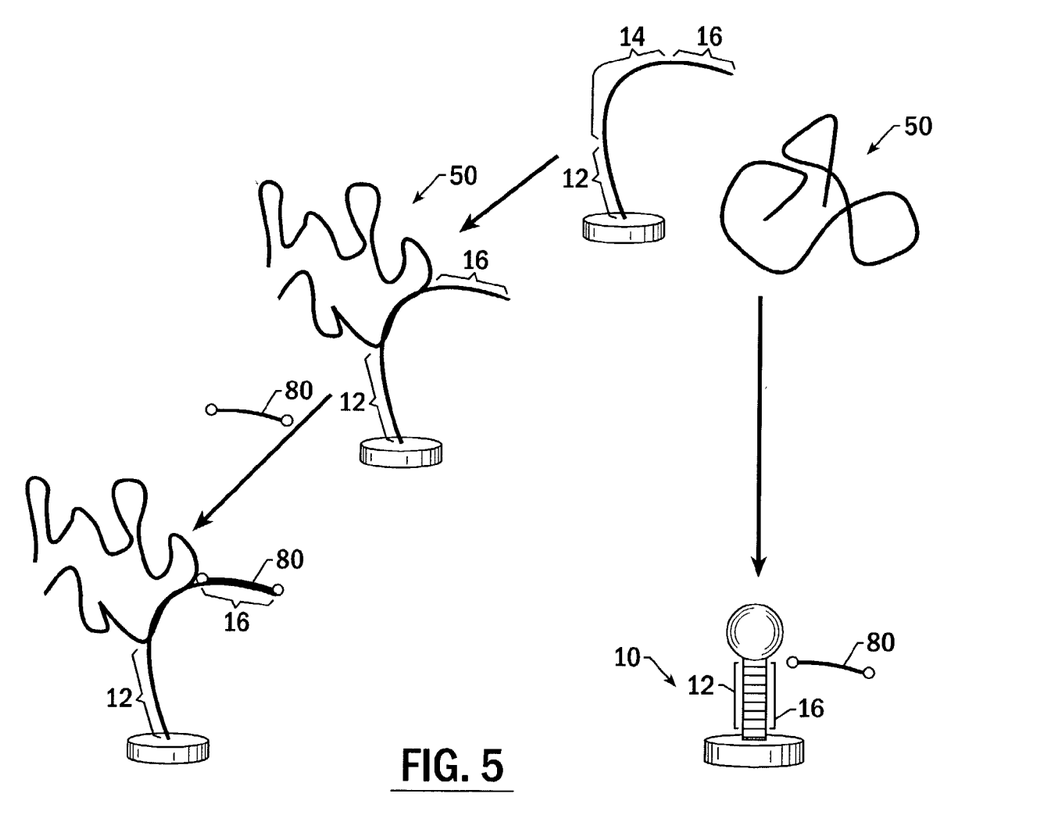
FIG. 5 is a graphic representation showing the interaction of the captor, target, and detector probe in accordance with an embodiment of the invention.

Referring to FIG. 5, after allowing the target sequence adequate time to hybridize with the captor, the temperature of the system is lowered to allow for the possible renaturation of the captor sequence into its prior hairpin conformation.

If a target nucleic acid 50 has hybridized with the loop portion 14 of a captor, the captor will not renature to the original hairpin shape due to the relatively large target sequence, which prevents the tails of the captor from encountering one another. This will leave the second tail 16 on the 3' end of the captor sequence exposed. The probe 80 is added to the system. Because the probe comprises a sequence which is complementary to the second tail sequence 16, and because the second tail sequence is exposed due to conjugation of the captor with the target, the probe 80 hybridizes with the second tail 16 of the captor.

If the target nucleic acid 50 has not hybridized with the loop portion 14 of the captor, the captor will be able to renature to the original hairpin shape upon cooling. Renaturing of the hairpin causes the first and second tails of the captor to hybridize to one another. The probe 80 is then added to the system. Again, the probe comprises a sequence which is complementary to the second tail sequence 16, and would normally tend to hybridize with the second tail sequence 16. However, because the second tail has already hybridized with the first tail 12 during the renaturing step, the probe 80 is unable to hybridize with the captor and is washed away.

Figure 6:
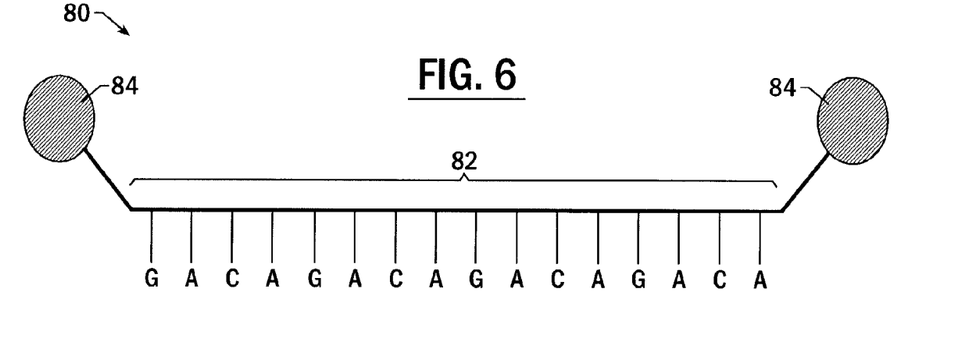
FIG. 6 is a representation of the detector probe in accordance with an embodiment of the invention.

Referring to FIG. 6, the universal detector probe 80 is a short segment of nucleic acid 82, From about 4 to about 24 nucleotides in length, preferably about 16. The sequence of the probe is complementary to at least a portion of the second tail of the captor, and the length of the probe sequence should be about the same length as the second tail, preferably 1 to 3 nucleotides shorter than the second tail. Referring again to FIG. 2, the exemplary probe of FIG. 6 is shown to have a sequence complementary to the second tail 16 shown in FIG. 2. Thus, in this example, the probe is readily capable of hybridizing with the second tail 16 of the captor.

The sequence of the probe is attached at one or both ends to a label molecule 84. The label molecule may be a fluorophore or a radioactive moiety which is detectable by instrumentation positioned outside of the system, ie. external to the sample being tested. Fluorophore labels such as fluorescein, Lucifer Yellow, erythrosine, tetramethylrhodamine, and coumarin are all commercially available fluorophores whose chemical structures are well known. More intense fluorescent probes such as quantum dots and phycobilipoproteins may also be used. Attachment of these fluorophores to nucleic acids is also known. A label is preferably attached to both ends of the detector probe, thereby emitting twice the signal of a detector probe having a single label. A particularly preferred fluorophore is 6-iodoacetamidofluoescin, a fluorescein derivative having the structure:

After exposure of the captor to the sample solution and to the probe, the captor is washed in buffer solution in order to remove any unhybridized probes. The resulting captors are analyzed, automatically or manually, for an increase in fluorescence or radioactivity, depending upon which type of label was used on the probe. Increased fluorescence or radioactivity indicates the presence of a probe upon the captor sequences, and therefore the presence of a target within the biological sample. We have for example been able to detect the presence of approximately 200 copies of a target RNA in 1 milliliter of sample using this method.

The selectivity for a particular target may be increased by simultaneously searching for more than one target sequence per target. This approach may be necessary if the target sequences are from viruses which tend to mutate rapidly. To this end, a cluster of captor molecules is preferably used, wherein the loop portions of the captors are each complementary to one of two or more target sequences present within the target nucleic acid. For each known target, a cluster of captors is prepared in which the loop sequences of the captors are preferably selected from one of the two to four complementary sequences, but in which the captors otherwise have the same spacer region 18, stem region 12,16, and connector region 22.

As used herein, a "cluster" is a multiplicity of captors each having loop sequences which may be the same or different, but each of which are complementary to a common target. The captors within a cluster all have identical tail sequences so that a universal detector probe may be used in conjunction with each of the captors.

An assay kit is provided by placing various captor clusters upon a common substrate. By maintaining several clusters upon the common substrate, multiple nucleic acid targets may be simultaneously detected and each of the targets may be distinctly identified.

Figure 7:
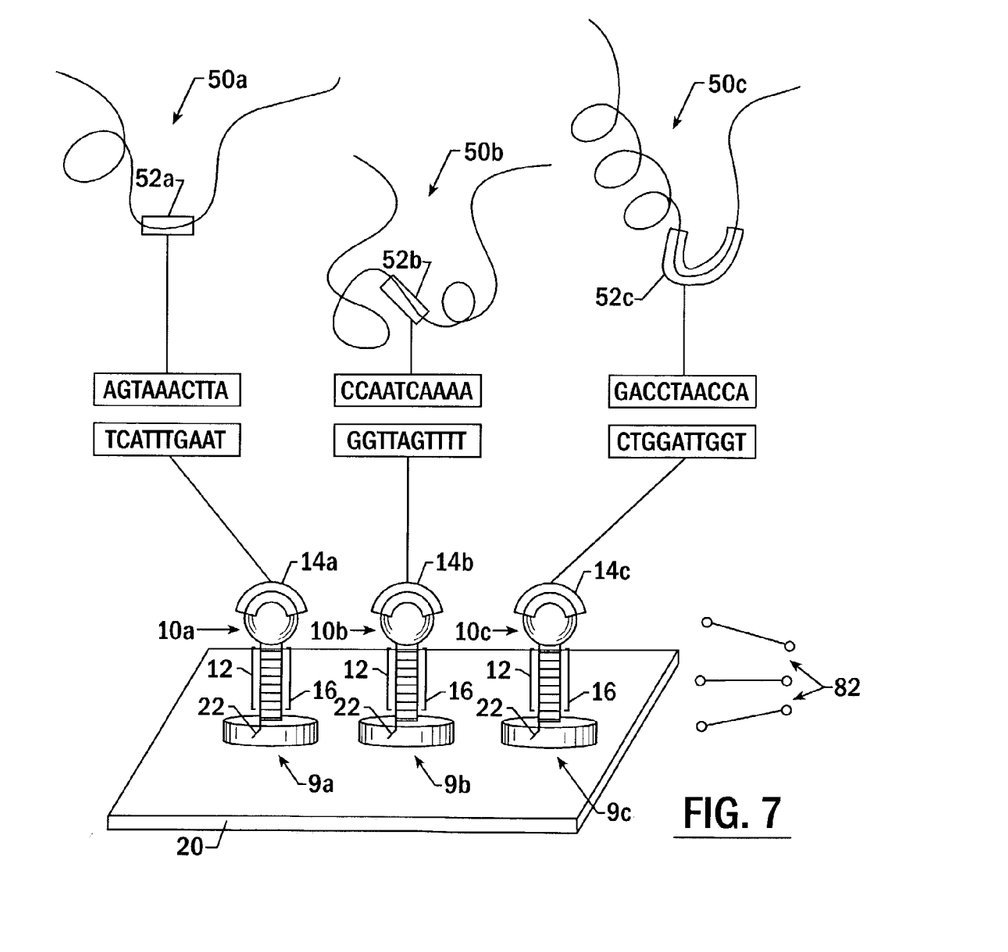
FIG. 7 illustrates a captor cluster array in accordance with an embodiment of the invention.

Referring to FIG. 7, an exemplary embodiment of the assay kit is shown wherein three different captor clusters 9a, 9b, 9c are positioned at three specific locations upon a common substrate 20. Captors of each cluster correspond to one of three suspected targets. For instance, all captors of the first cluster 9a correspond to a first target 50a, all captors of the second cluster 9b correspond to a second target 50b, and all captors of the third cluster 9c correspond to a third target 50c. If and only if the loop sequences 14 of the captors within a particular cluster become hybridized to their corresponding target do those captors become available for attachment to detector probes. Thus, only those regions upon the common substrate 20 having a cluster with target-laden captors will subsequently bind to a probe and exhibit increased fluorescence. In this manner, several different targets may be identified simultaneously.

Still referring to FIG. 7, by way of example, captors of clusters 9a, 9b, and 9c are illustrated as having respective captor sequences of:

```
TCATT TGAAT,         (Seq.ID.13)

GGTTA GTTTT,         (Seq.ID.15)
and

CTGGA TTGGT.         (Seq.ID.17)
``` which are complementary to target sequences 52a, 52b, and 52c, respectively, illustrated as

```
AGTAA ACTTA,         (Seq.ID.12)

CCAAT CAAAA,         (Seq.ID.14)
and

GACCT AACCA.         (Seq.ID.16)
```

When using the captors in an assay situation, it is preferable that the stem regions of the captor sequences be the same for all captors of the array. This allows the use of a universal detector probe 80, meaning that probes 80 having an identical sequence may be used with all captors of the assay. Because the probe is complementary to the second tail 16 of the captor, and the probes ability to attach to the captor is subject only to the availability of the second tail, a universal detector probe may be used in conjunction with captors having varying loop sequences. For instance, in FIG. 7, the first tail 12 and second tail 16 of each captor may be identical, and all probes 80 used with the assay are also identical.

The ability to indicate the presence of several different targets within a sample using identical probes 80 is favorable from a cost standpoint because it eliminates the need to manufacture and package several different types of probes. The universal probe also greatly simplifies the use of the assay, since an almost unlimited number of targets can be identified simultaneously by exposing the various captors to the sample and then exposing the captors to a solution containing multiple universal probes.

The detector and detection method provide an improved ability to detect the presence of nucleic acid targets within a biological sample. An assay using the described captors is able to detect targets without the need to amplify the targets, such as by PCR. Many prior techniques analyzed targets within a volume of solution. Because it was difficult to detect labels within a solution, amplification was required. Since the presence of targets are indicated by labeled probes bound by captors in a specific location on the surface of a substrate rather than within a volume of liquid, a much lower signal from the label can be detected and amplification is not needed.

Problems associated with signal noise have also been overcome. Prior detectors used complementary label-quencher molecules which emitted a signal having a strength indicating whether the detector had become hybridized to a target or not. The difference in magnitude of the detector signal was often hard to detect against background noise and interference. With the detector and method, a label is or is not attached to the captor depending upon if the target is or is not present within the sample. Thus, the detector probes either do or do not emit a signal from the captor. The necessity of detecting variances in signal strength is avoided.

EXAMPLES

In order to demonstrate the practice and utility of the method and probe, the Satellite Tobacco Mosaic Virus (STMV) was chosen as a model system for testing the concept of the method and probe. STMV is a icosahedral particle with a diameter of approximately 17 nm containing a single-stranded RNA genome. Referring to (Seq. ID. 4) in FIG. 8, the RNA core is comprised of 1059 nucleotides and is encapsidated by 60 identical copies of a 159 amino acid coat protein. The intact STMV structure has been determined to 1.8 Å resolution by x-ray crystallography revealing more than half of the single-stranded genome to self-fold upon itself to form helical segments.

Example 1

Selection of Target Sequences

Three different target sequences were selected from the STMV genome. These regions were known to be necessary for viral replication. Complements to the three sequences were then determined for use as loop sequences within captors. The loop sequences were

```
3'-ATGTA TAACG GAAGA AGATG TTCTC-5',   (Seq.ID.5)

3'-AATTT AGCTG CCCAC TGTTA AGCTT A-5', (Seq.ID.6)

3'-AGCGT ATGCA ATCAC ACTGA TGGCA A-5', (Seq.ID.7)
```

Example 2

Preparation of Captor

Referring to items 1 through 3 in FIG. 9, three captor sequences, each including one of the three selected loop sequences was constructed. Each of the captors was constructed having a first tail region comprising four repeat CTGT tetramers, a spacer group of four adenosine residues, the loop region, and a second tail region comprising ACAG tetramers. An amine group was attached to the 5' end of each captor for use in subsequent bonding to a substrate. These three captor sequences are simply referred to as 1, 2 and 3 and were ordered as designed from Qiagen Operon, Alameda, Calif.

Example 3

Preparation of Detector Probe

Referring to item 4 in FIG. 9, an oligonucleotide probe sequence was designed to be complementary to the second tail sequence of the captor from Example 2. The probe was ordered commercially with thiol endgroups. The oligonucleotide probe was dissolved in 100 mM Tris buffer at a pH of 7.0. The disulfide bond was then cleaved by the addition of 50 mM DTT (dithiothreitol) by incubation for another 30 minutes. A fluorescent molecule, 6-iodoacetamidofluorescein was then added and allowed to react for 2 hours to allow for maximal coupling. This step is known to be very efficient and most of the oligonucleotides react to form the fluresceinated derivative.

Example 4

Binding Captors to Substrate

Filter paper was used as a substrate and functionalized with aldehyde groups by soaking in formaldehyde and drying overnight. The captor sequences of Example 2 were obtained as lyophilized powders and resuspended in DEPC (diethyl pyrocarbonate) treated water and spotted in microliter amounts on the functionalized surfaces. DEPC is a chemical that inactivates RNAses and DNAses.

Figure 10:
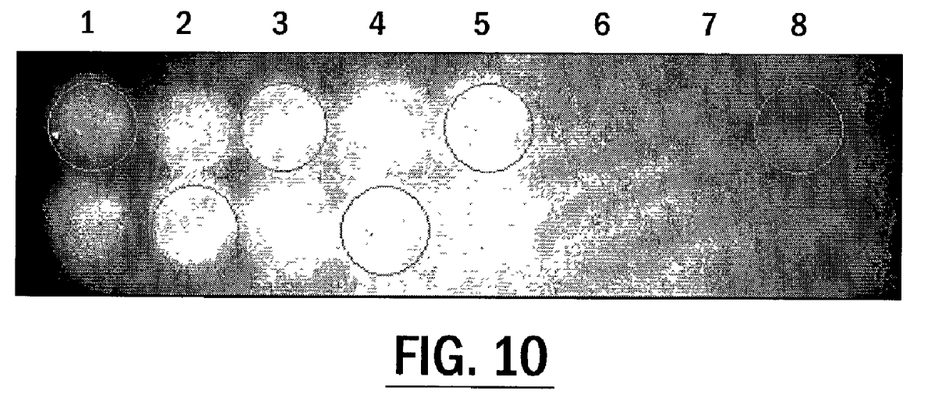
FIG. 10 is substrate having various captor clusters adhered thereto where the captors have been exposed to varying concentrations of target molecules and subsequently exposed to detector probes in accordance with an embodiment of the invention.

Referring to FIG. 10, an equal proportion of captors 1, 2, and 3 were spotted in dual 8 lane clusters upon the substrate. Each spot had the same amount of the captor sequence. The concentration of the captors in the solution was 200 micromolar. The binding efficiency of the captors to the functionalized surfaces were approximately 60 percent and thus each spot had between $1.204 \times 10^{15}$ and $1.204 \times 10^{16}$ captor molecules. After adding the captor sequence(s) to different spots on the functionalized substrate, the substrate was allowed to dry in air for about an hour. The substrate was then washed thoroughly in distilled water and dried again.

Example 5

Denaturing and Exposure of Captor to Target Sequence and Samples Lacking Target Sequences After drying of the captor-laden substrate of Example 4, the substrate and the STMV RNA were denatured by heating to 65° C. Lanes 1-5 of the substrate were contacted with STMV RNA at a concentration of 0.5 µM, 1.0 µM, 1.5 µM, 2.0 µM, 3.0 µM, respectively. For comparison, lanes 6-8 were contacted with $tRNA^{Phe}$ (40.73 mM), mRNA E. Coli (22.6 µM), and mRNA human (35.92 µM), respectively.

Example 6

Addition of Detector Probe

A solution containing the detector probes of Example 3 was added to the substrate. The detector probes were provided as 10 µM of lyophilized powder dissolved in 0.1 mL of Tris-HCL at a pH of 7.0. The detection solution contains 0.1 mL of the probe solution and 0.9 mL of 10 mM NaCl. The detection solution was applied evenly to the substrate.

Example 7

Detection of Target Nucleic Acid

Figure 11:
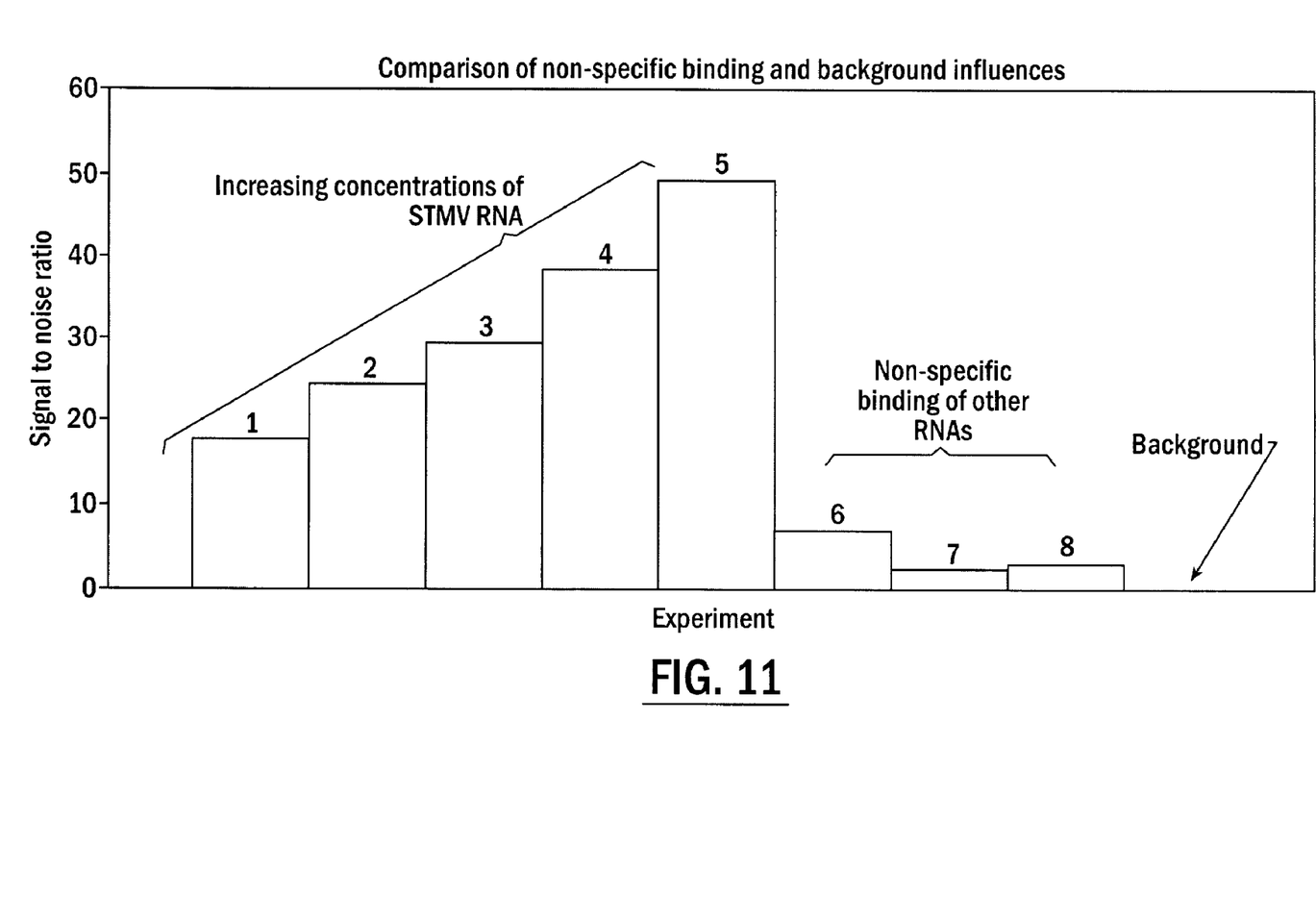
FIG. 11 is a chart showing the fluorescence of the captor clusters in response to exposure to various combinations of targets in accordance with an embodiment of the invention.

Referring again to FIG. 10 and also to FIG. 11, the captors and/or captor-target conjugates of the substrate of Example 6 were analyzed using a Nikon™ Eclipse E600 laboratory fluoroscope with the Nikon™ 10× DICH lens and a ND8 filter. Fluorescence intensities from each spot were recorded and charted.

As demonstrated in FIG. 11, the fluorescent intensity of the probes was much greater for samples that had the target STMV RNA sequence, showing that the detection method properly identified the presence of the target. The intensities indicated on the bar chart are average intensities calculated by 20 different measurements from each spot on the substrate. Note, the increase in fluorescence does not necessarily increase linearly with increased target concentration. As seen in samples 6-8, fluorescence of the detector did not increase substantially in the absence of the target sequences, even after the captors were contacted with high concentrations of non-target RNA. Thus, the detector clearly distinguishes between target and non-target sequences within a sample.

Many modifications and other embodiments of the inventions set forth herein will come to mind to one skilled in the art to which these inventions pertain having the benefit of the teachings presented in the forgegoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. A method of detecting the presence of a nucleic acid target within a biological sample comprising the steps of:
supplying a substrate-bound, hairpin-shaped nucleic acid captor;
contacting the captor with a suspected target under conditions favorable for denaturing of the captor;
placing the captor under conditions favorable for renaturing prior to contacting the captor with a labeled detector probe;
contacting the captor with the labeled detector probe;
washing the captor; and
determining if the labeled detector probe remains adhered to the captor, thereby detecting the presence of the nucleic acid target.

2. The method of claim 1 wherein the captor is bound to the substrate at its 5' terminus, and wherein the captor sequence serially comprises, from the 5' terminus to the 3' terminus,
a first tail sequence,
an optional first spacer sequence,
a loop sequence that is complementary to a sequence within the target,
an optional second spacer sequence, and
a second tail sequence that is complementary to the first tail sequence.

3. The method of claim 2 wherein the tail sequences comprise a series of four repeat tetramers, wherein the tail sequences are not complementary to the target.

4. The method of claim 2 wherein the tail sequences are between 8 and 20 residues in length, the loop sequence is between about 10 and 40 residues in length, and the optional spacer sequences are from 0 to 10 nucleotides in length.

5. The method of claim 2 wherein the captor and detector probe comprise DNA, RNA, PNA, or a combination thereof.

6. The method of claim 1 wherein denaturing comprises raising the temperature of the captor above a critical temperature.

7. The method of claim 1 wherein the suspected target is presented within a heterogeneous biological sample.

8. The method of claim 1 wherein the step of placing the captor under conditions favorable for renaturing comprises lowering the temperature of the captor below a critical temperature.

9. The method of claim 1 wherein the captor is denatured and placed under conditions for renaturing while maintained in a buffer solution.

10. The method of claim 1 wherein the suspected target is maintained in a medium prior to contact with the captor, and wherein the medium is treated with nuclease inhibitors prior to contact of the suspected target with the captor.

11. The method of claim 10 wherein the nuclease inhibitor is selected from the group consisting of sodium dodecyl sulfate (SDS), ethylene diamine tetraacetic acid (EDTA), dimethyl sulfoxide (DMSO), and combinations thereof.

12. The method of claim 1 wherein the detector probe is labeled with a molecule selected from the group consisting of fluorophores and radioisotopes.

13. The method of claim 12 wherein the detector probe is labeled with a fluorophore and the presence of the probe upon the captor is determined with a fluoroscope.

14. A method of detecting the presence of a nucleic acid target within a biological sample comprising the steps of:
supplying a single-stranded nucleic acid captor sequence that is bound to a substrate at its 5' terminus, wherein the captor sequence serially comprises, from the 5' terminus to the 3' terminus,
a first tail sequence,
an optional first spacer sequence,
a loop sequence that is complementary to a sequence within the target,
an optional second spacer sequence, and
a second tail sequence that is complementary to the first tail sequence;
denaturing the captor sequence;
contacting the captor sequence with the biological sample, whereby targets within the sample tend to hybridize with the loop sequence of the captor;
placing the captor sequence under conditions favorable for renaturing the captor prior to contacting the captor with a labeled detector probe, whereby the first and second tail sequences tend to hybridize to one another if not hindered by a target sequence;
contacting the captor with the labeled detector probe that is complementary to the second tail sequence of the captor;
washing the captor; and
detecting the presence of labeled detector probes remaining upon the captor after the washing step, whereby the presence of the labeled probes indicates the presence of the target within the sample.

15. A method of detecting the presence or absence of multiple nucleic acid targets within a biological sample comprising the steps of:
supplying multiple single-stranded nucleic acid captors, wherein each captor comprises, from the 5' terminus to the 3' terminus,
a first tail sequence,
an optional first spacer sequence,
a loop sequence that is complementary to a sequence within a target,
an optional second spacer sequence, and
a second tail sequence that is complementary to the first tail sequence;
grouping the multiple captors into clusters such that all captors of a common cluster have a loop sequence complementary to a common target;
disposing the captor clusters upon a substrate;
contacting the captors with the biological sample under conditions favorable for denaturing of the captors, whereby targets within the sample tend to hybridize captors having loop sequences that are complementary to sequences within the targets;
placing the captors under conditions favorable for renaturing prior to contacting the captors with a labeled universal detector probe, whereby the first and second tail sequences tend to hybridize to one another if not hindered by a target sequence;
contacting the captors with labeled universal detector probes that are complementary to the second tail sequences of each captor;
washing the captors; and
detecting the presence of labeled detector probes remaining upon the captors after the washing step, whereby the presence of the labeled probes in a particular cluster of captors indicates the presence of the target having a sequence complementary to the loop portion of the captors of that cluster.

16. The method of claim 15 wherein all captors have a common second tail sequence and wherein the universal detector probes all contain a common nucleic acid sequence.

* * * * *

SEQUENCE LISTING

<160> NUMBER OF SEQ ID NOS: 17

<210> SEQ ID NO 1
<211> LENGTH: 26
<212> TYPE: DNA
<213> ORGANISM: Artificial Sequence
<220> FEATURE:
<223> OTHER INFORMATION: The loop portion of an exemplary nucleic acid
      captor molecule.

<400> SEQUENCE: 1
gactgaaggc ctctttgtag aagaag                                          26

<210> SEQ ID NO 2
<211> LENGTH: 16
<212> TYPE: DNA
<213> ORGANISM: Artificial Sequence
<220> FEATURE:
<223> OTHER INFORMATION: The tail portion of an exemplary nucleic acid
      captor molecule.

<400> SEQUENCE: 2
gacagacaga cagaca                                                     16

<210> SEQ ID NO 3
<211> LENGTH: 16
<212> TYPE: DNA
<213> ORGANISM: Artificial Sequence
<220> FEATURE:
<223> OTHER INFORMATION: The tail portion of an exemplary nucleic acid
      captor molecule.

<400> SEQUENCE: 3
tgtctgtctg tctgtc                                                     16

<210> SEQ ID NO 4
<211> LENGTH: 1058
<212> TYPE: DNA
<213> ORGANISM: Satellite Tobacco Mosaic Virus

<400> SEQUENCE: 4
agtaaactta ccaatcaaaa gacctaacca acaggactgt cgtggtcatt tatgctgttg     60
ggggacatag ggggaaaaca tattgccttc ttctacaaga ggccttcagt cgccataatt    120
acttggcgcc caattttggg tttcagttgc tgtttccagc tatggggaga ggtaaggtta    180
aaccaaaccg taaatcgacg ggtgacaatt cgaatgttgt tactatgatt agagctggaa    240
gctatcctaa ggtcaatccg actccaacgt gggtcagagc catacctttc gaagtgtcag    300
ttcaatctgg tattgctttt aaagtaccgg tcgggtcact attttcggca aatttccgga    360
cagattcctt tacaagcgtc acagtgatga gtgtccgtgc ttggacccag ttaacaccgc    420
cagtaaatga gtacagtttt gtgaggctga agccattgtt caagactggt gactctactg    480
aggagttcga agggcgtgca tcaaacatca acacacgagc ttctgtaggg tacaggattc    540
caactaattt gcgtcagaat actgtggcag ccgacaatgt atgcgaagta agaagcaact    600
gtcgacaagt cgccttggtt atttcgtgtt gttttaactg aacctcgaca taagcctttt    660
ggatcgaagg ttaaacgatc cgctcctcgc ttgagcttga ggcggcgtat ctcttatgtc    720
aacagagaca ctttggtcta tggttgtata acaatagata gactcccgtt tgcaagatta    780
gggttaacag atcttgccgt tagtctggtt agcgcgtaac cggccttgat ttatggaata    840

```
gatccattgt ccaatggctt tgccaatgga acgccgacgt ggctgtataa tacgtcgttg      900
acaagtacga aatcttgtta gtgttttttcc ctccacttaa atcgaagggt tttgttttgg      960
tcttcccgaa cgcatacgtt agtgtgacta ccgttgttcg aaacaagtaa aacaggaagg     1020
gggttcgaat ccctccctaa ccgcgggtaa gcggccca                             1058

<210> SEQ ID NO 5
<211> LENGTH: 25
<212> TYPE: DNA
<213> ORGANISM: Artificial Sequence
<220> FEATURE:
<223> OTHER INFORMATION: Artificial sequence designed to be
      complementary to the STMV virus.

<400> SEQUENCE: 5
ctcttgtaga agaaggcaat atgta                                             25

<210> SEQ ID NO 6
<211> LENGTH: 26
<212> TYPE: DNA
<213> ORGANISM: Artificial Sequence
<220> FEATURE:
<223> OTHER INFORMATION: Artificial sequence designed to be
      complementary to the STMV virus.

<400> SEQUENCE: 6
attcgaattg tcacccgtcg atttaa                                          26

<210> SEQ ID NO 7
<211> LENGTH: 26
<212> TYPE: DNA
<213> ORGANISM: Artificial Sequence
<220> FEATURE:
<223> OTHER INFORMATION: Artificial sequence designed to be
      complementary to the STMV virus.

<400> SEQUENCE: 7
aacggtagtc acactaacgt atgcga                                          26

<210> SEQ ID NO 8
<211> LENGTH: 61
<212> TYPE: DNA
<213> ORGANISM: Artificial Sequence
<220> FEATURE:
<223> OTHER INFORMATION: Artificial sequence designed to be
      complementary to the STMV.

<400> SEQUENCE: 8
ctgtctgtct gtctgtaaaa ctcttgtaga agaaggcaat atgtacagac agacagacag     60
a                                                                     61

<210> SEQ ID NO 9
<211> LENGTH: 62
<212> TYPE: DNA
<213> ORGANISM: Artificial Sequence
<220> FEATURE:
<223> OTHER INFORMATION: Artificial sequence designed to be
      complementary to the STMV.

<400> SEQUENCE: 9
ctgtctgtct gtctgtaaaa attcgaattg tcacccgtcg atttaacaga cagacagaca     60
ga                                                                    62

<210> SEQ ID NO 10
```

```
<211> LENGTH: 62
<212> TYPE: DNA
<213> ORGANISM: Artificial Sequence
<220> FEATURE:
<223> OTHER INFORMATION: Artificial sequence designed to be
      complementary to the STMV.

<400> SEQUENCE: 10
ctgtctgtct gtctgtaaaa aacggtagtc acactaacgt atgcgacaga cagacagaca    60
ga                                                                   62

<210> SEQ ID NO 11
<211> LENGTH: 16
<212> TYPE: DNA
<213> ORGANISM: Artificial Sequence
<220> FEATURE:
<223> OTHER INFORMATION: Artificial sequence designed to be
      complementary to the STMV.

<400> SEQUENCE: 11
ctgtctgtct gtctgt                                                    16

<210> SEQ ID NO 12
<211> LENGTH: 10
<212> TYPE: DNA
<213> ORGANISM: Artificial Sequence
<220> FEATURE:
<223> OTHER INFORMATION: Hypothetical target sequence.

<400> SEQUENCE: 12
attcaaatga                                                           10

<210> SEQ ID NO 13
<211> LENGTH: 10
<212> TYPE: DNA
<213> ORGANISM: Artificial Sequence
<220> FEATURE:
<223> OTHER INFORMATION: Compliment to hypothetical target sequence in
      SEQ ID NO. 12

<400> SEQUENCE: 13
tcatttgaat                                                           10

<210> SEQ ID NO 14
<211> LENGTH: 10
<212> TYPE: DNA
<213> ORGANISM: Artificial Sequence
<220> FEATURE:
<223> OTHER INFORMATION: Hypothetical target sequence.

<400> SEQUENCE: 14
aaaactaacc                                                           10

<210> SEQ ID NO 15
<211> LENGTH: 10
<212> TYPE: DNA
<213> ORGANISM: Artificial Sequence
<220> FEATURE:
<223> OTHER INFORMATION: Compliment to hypothetical target sequence in
      SEQ ID NO. 14.

<400> SEQUENCE: 15
ggttagtttt                                                           10

<210> SEQ ID NO 16
<211> LENGTH: 10
```

```
-continued

<212> TYPE: DNA
<213> ORGANISM: Artificial Sequence
<220> FEATURE:
<223> OTHER INFORMATION: Hypothetical target sequence.

<400> SEQUENCE: 16
accaatccag                                                              10

<210> SEQ ID NO 17
<211> LENGTH: 10
<212> TYPE: DNA
<213> ORGANISM: Artificial Sequence
<220> FEATURE:
<223> OTHER INFORMATION: Compliment to hypothetical target sequence in
      SEQ ID NO. 16.

<400> SEQUENCE: 17
ctggattggt                                                              10
```